(12) United States Patent
Borchard

(10) Patent No.: US 6,382,212 B1
(45) Date of Patent: May 7, 2002

(54) FENESTRATED SURGICAL DRAPE WITH IN SITU FEATURES

(75) Inventor: Craig F. Borchard, Mendota Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/483,871

(22) Filed: Jan. 18, 2000

(51) Int. Cl.[7] .............................................. A61B 19/00
(52) U.S. Cl. ...................................... 128/849; 128/853
(58) Field of Search ................... 128/849–856

(56) References Cited

U.S. PATENT DOCUMENTS

| | | | |
|---|---|---|---|
| 3,799,161 A | * 3/1974 | Collins | 128/132 |
| 3,923,052 A | * 12/1975 | Zoephel | 128/853 |
| 4,024,862 A | 5/1977 | Collins | 128/132 |
| 4,080,963 A | * 3/1978 | Merry | 128/853 |
| 4,316,455 A | * 2/1982 | Stoneback | 128/853 |
| 5,074,316 A | 12/1991 | Dowdy | 128/849 |
| 5,339,831 A | 8/1994 | Thompson | 128/852 |
| 5,445,165 A | 8/1995 | Fenwick | 128/849 |
| 5,452,729 A | 9/1995 | Bergsbaken et al. | 128/849 |
| 6,105,579 A | * 8/2000 | Levitt | 128/853 |

* cited by examiner

Primary Examiner—Michael A. Brown
(74) Attorney, Agent, or Firm—Thomas G. Berry; Eric R. Waldkoetter

(57) ABSTRACT

A fenestrated surgical drape has a panel having at least two portions and a centrally located fenestration. The two portions each have a deployment tab located on a portion distal end and the portions are folded near or on the fenestration so that the deployment tab is accessible and adapted to deploy the portion away from the fenestration. The portions are folded over the fenestration so that the inner surface surrounding the fenestration is unobstructed for ease in locating the fenestration over a patient application site.

26 Claims, 7 Drawing Sheets

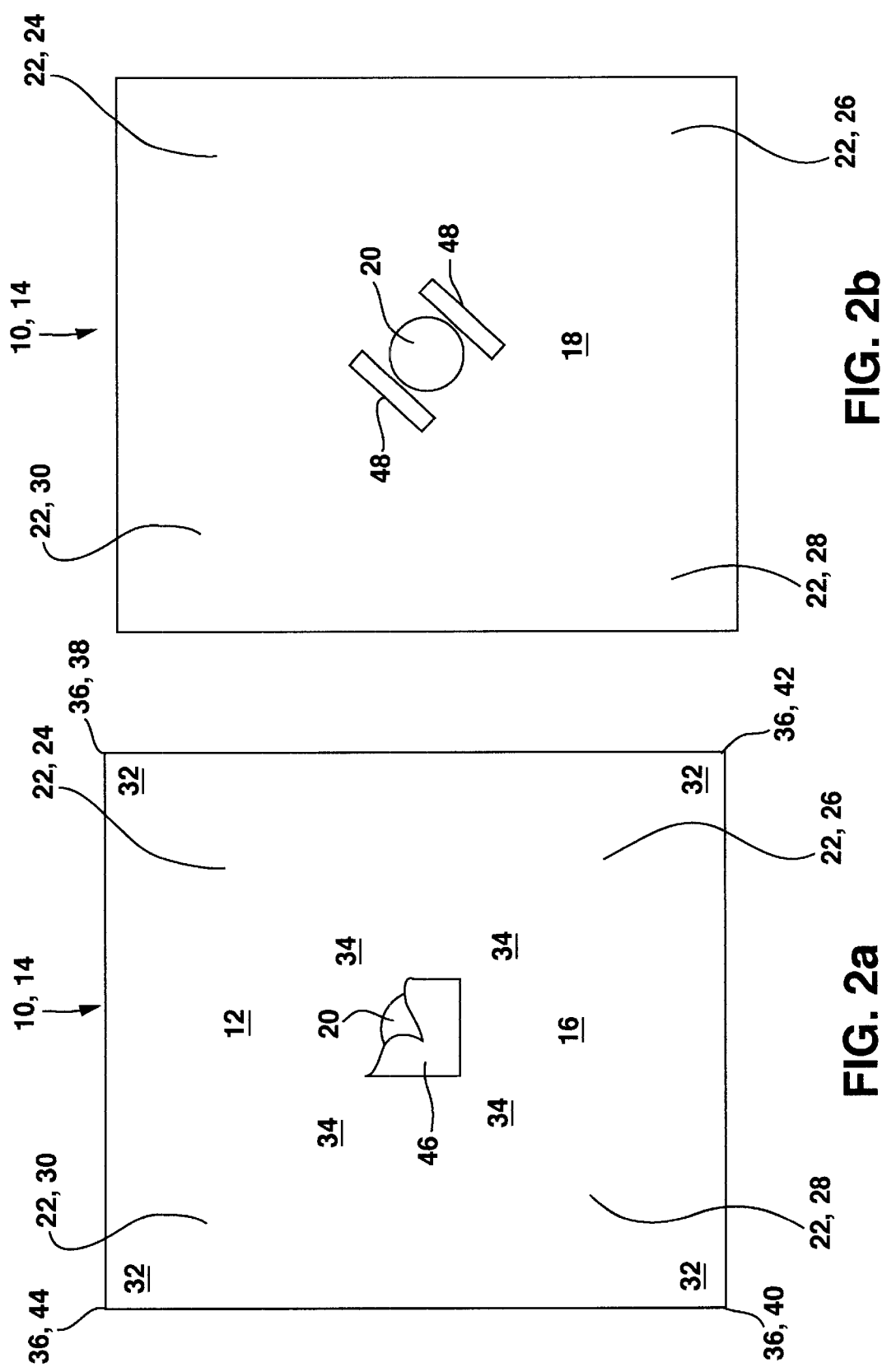

FENESTRATED SURGICAL DRAPE WITH IN SITU FEATURES

BACKGROUND OF THE INVENTION

This disclosure relates to a surgical drape and more specifically to a surgical drape used in conjunction with an implantable medical device.

The medical device industry produces a wide variety of electronic and mechanical devices for treating patient medical conditions. Depending upon the medical condition, medical devices can be surgically implanted, connected externally to the patient receiving treatment, or used during surgery. Clinicians use medical devices alone or in combination with drug therapies and surgery to treat patient medical conditions. For some medical conditions, medical devices provide the best, and sometimes the only, therapy to treat a medical condition and restore an individual to a more healthful condition and a fuller life. When medical devices are used, attached, implanted or serviced, clinicians often use a fenestrated surgical drape during the procedure.

Fenestrated surgical drapes are used to maintain sterile conditions, maintain patient privacy, absorb fluid, and provide a clear and clean work area for the clinician. A fenestration is an opening in the surgical drape that provides the clinician with access to a desired site on the patient's body while preserving the function of the surgical drape for other areas of the patient's body. Surgical drapes are typically used in clinician's offices and operating rooms where the clinician is engaged in a variety of tasks related to the use of the surgical drape such as monitoring the patient's condition with instruments, administering therapeutic agents to the patient, and instructing assistants such as nurses to perform a multitude of tasks. Often the surgical drape is used while the patient is conscious when it is particularly important to maintain the confidence and trust of the patient, so the patient cooperates with the procedure to be performed. Mistakes under these conditions can complicate the procedure being performed and can increase the patient's health risk.

To accomplish their purpose, surgical drapes are often large enough to require folding for storage and handling convenience. Folded surgical drapes can be difficult to place in situ on the desired patient application site because the surgical drape requires preparation before placement. Folded surgical drapes can be difficult to deploy because the surgical drape is not folded in a manner to facilitate unfolding when placed on the desired patient application site. The additional handing of surgical drapes to place the drape over the desired application site and the difficulty in unfolding the drape is inconvenient, time consuming, increases the likelihood for mistakes, and makes maintaining sterile conditions difficult.

SUMMARY OF THE INVENTION

A surgical drape having a panel with at least two portions is folded over a fenestration so that the inner surface to be placed on the patient surrounding the fenestration is unobstructed by the portions for ease of locating the fenestration over the application site. In another version of the invention, a deployment tab is located on each of the at least two portion's distal end and the portions are folded near or on the fenestration so that the deployment tab is accessible and adapted to unfold the portion away from the fenestration.

BRIEF DESCRIPTION OF THE DRAWINGS

FIGS. 2a–b show the surgical drape unfolded;

DETAILED DESCRIPTION

Figure 1:
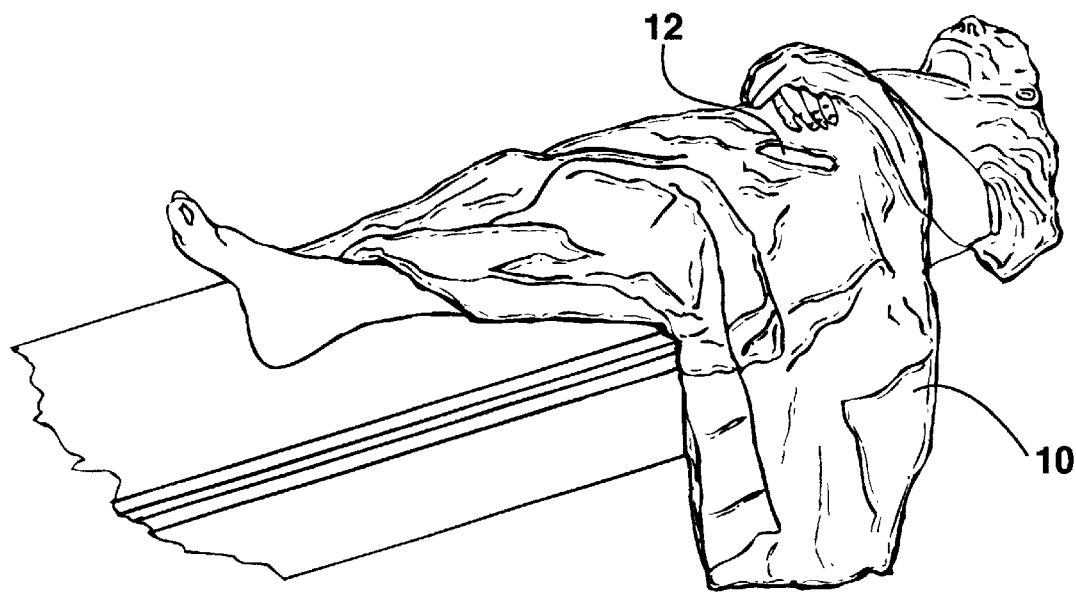
FIG. 1 shows an environment for a surgical drape.

FIG. 1 shows the environment of a surgical drape. The fenestrated surgical drape with in situ features 10 can be used in a wide range of treatment situations such as surgery, medical device implantation procedures, and medical device servicing procedures. An example of a medical device that requires implantation and servicing is an implantable drug deliver pump (not shown) that requires periodic refills. A surgical drape with in situ features 10 refers to use directly on a patient application site 12. The surgical drape 10 provides a sterile and clear working surface for the clinician performing the procedure. The surgical drape also assists in maintaining the patient modesty, comfort, and relaxation.

Figure 3A:
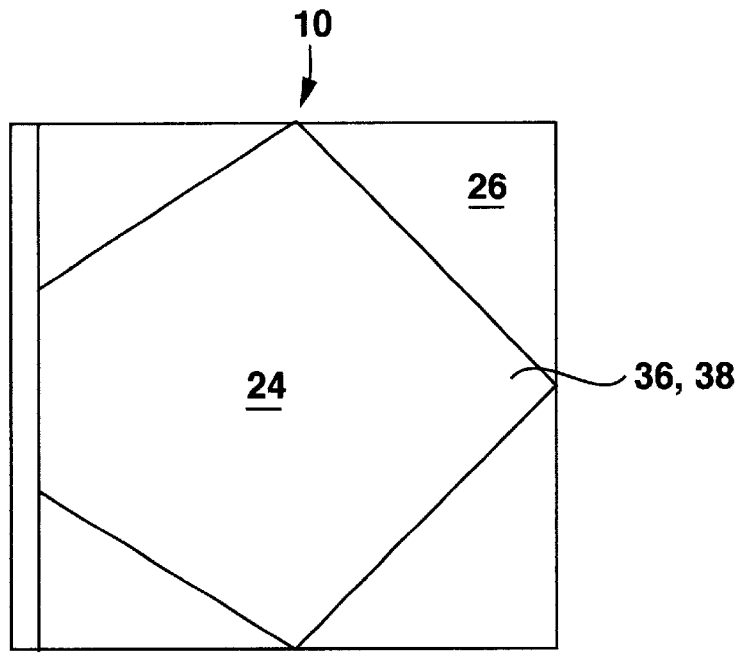
FIGS. 3a–b show the surgical drape folded.

FIG. 2a shows the surgical drape 10 outer surface and FIG. 2b shows the inner surface. The surgical drape 10 comprises a panel 14 having an outer surface 16, an inner surface 18, and a centrally located fenestration 20 in the panel 14. The panel 14 is composed of at least two portions 22 more specifically a first portion 24 and a second portion 26, and can include a third portion 28, a fourth portion 30, and additional portions. Each of the portions 22 has a distal end 32 near the periphery of the panel 14, a proximal end 34 near the fenestration 20, and a deployment tab 36 located on the portion distal end 32. The deployment tab 36 for each portion 22 is configured as a first deployment tab 38, a second deployment tab 40, a third deployment tab 42, and a fourth deployment tab 44. The deployment tab 36 for each portion 22 is adapted to deploy the portion 22 away from the fenestration 20 (FIG. 3a). The panel 14 can take a wide variety of shapes such as a tetragon, and the panel 14 is sized for the intended procedure such as a 76.2 cm (30.0 in) tetragon square used for refilling a drug deliver pump. The outer surface 16 is composed of a material suitable for surgery such as Dexter Absorbent Blue available from B. Braun Medical. The inner surface 18 is also composed of a material suitable for surgery such as used for the outer surface 16, and can be coated with a thin nonabsorbent material such as a plastic polycoat to prevent or reduce the transfer of fluids across panel 14. The fenestration 20 is an opening in the panel 14 sized for the intended procedure. The fenestration 20 can be sized for a medical device such as a 8.9 cm (3.5 in) circular opening for refilling a drug deliver pump. Although the fenestration 20 is generally centrally located in the panel 14, the fenestration 20 can be placed off center in the panel 14. The fenestration 20 can also have a fenestration cover 46 that covers the fenestration 20 to aid in maintaining sterility and patient modesty until the clinician is ready to perform the desired procedure. An adhesive 48 placed on the inner surface 18 near the fenestration 20 is a type compatible with surgical use and amount sufficient to attach the surgical drape to the patient in a manner desired by the clinician. For example, the adhesive 48 can be at least one adhesive strip or more strips manufactured from a material such as 3M® tape 9889.

Figure 3B:
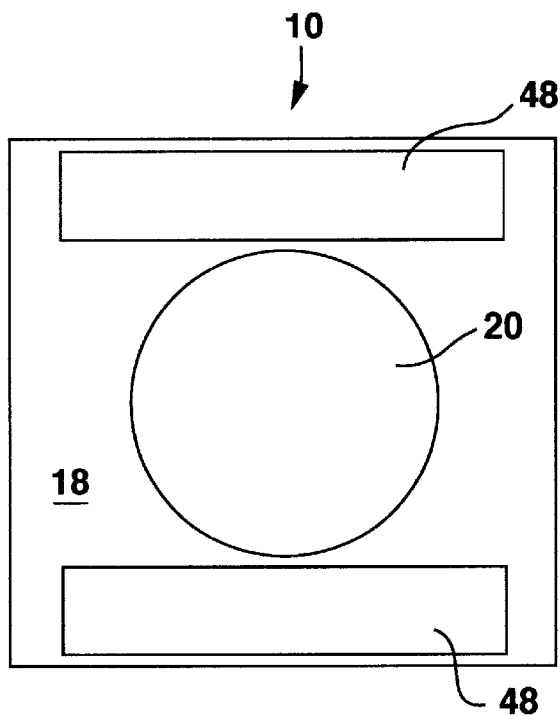

FIG. 3a shows an outer, away from the patient, view of a folded surgical drape 10, and FIG. 3b shows an inner, toward the patient, view of a folded surgical drape 10. The surgical drape 10 is folded in a compact form for ease of handing so that it is ready for deployment without the need for additional preparation. FIG. 3a shows the first 24 and second portions 26 folded over the fenestration 20 with the first deployment tab 38 presented for grasping. The first portion 24 and the second portion 26 are folded so that the second portion 26 is located over the fenestration 20 and the first portion 24 is located over the second portion 26. Once folded, the portions 22 typically remain folded over the fenestration 20 until after the fenestration 20 is placed over the application site 12. FIG. 3b shows the inner surface 18 surrounding the fenestration 20 is unobstructed for ease in locating the fenestration 20 over an application site 12. Additionally, adhesive 48 adjacent to the fenestration are shown for attaching the surgical drape 10 to the application site 12. Sterility of the surgical drape 10 is substantially maintained until the portions 22 are deployed.

Figure 4:
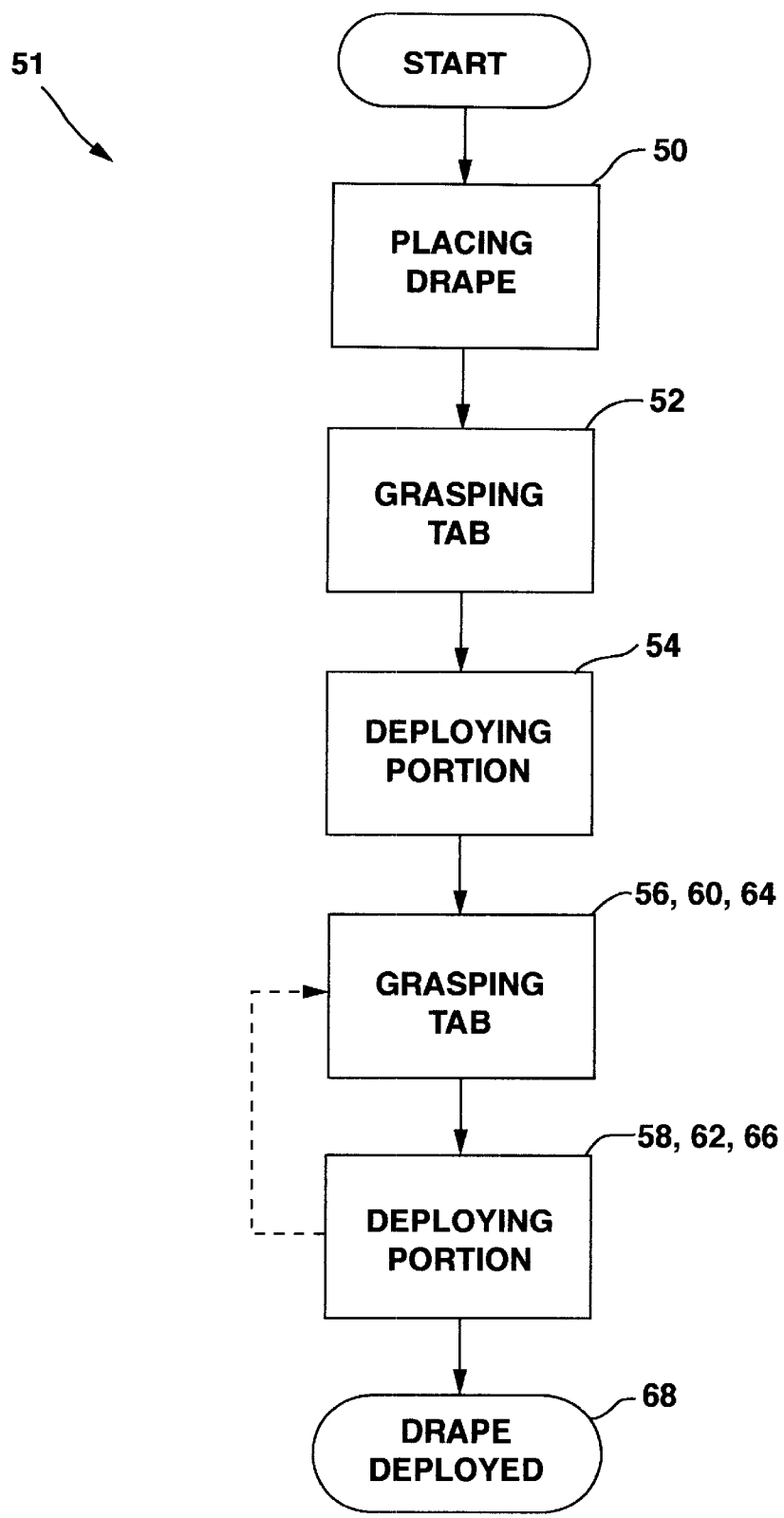
FIG. 4 shows a method for surgical drape deployment.
Figure 5A:
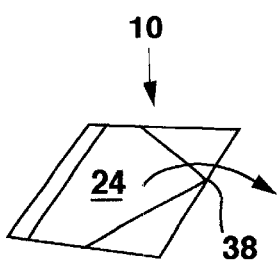
FIGS. 5a–f show a sequence for surgical drape deployment.
Figure 5B:
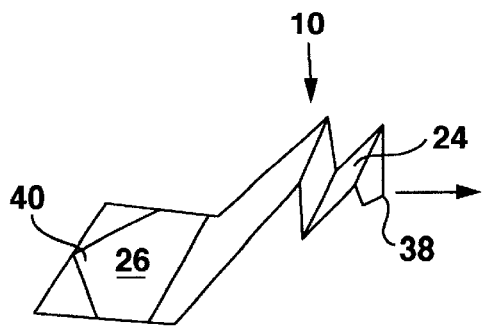
Figure 5C:
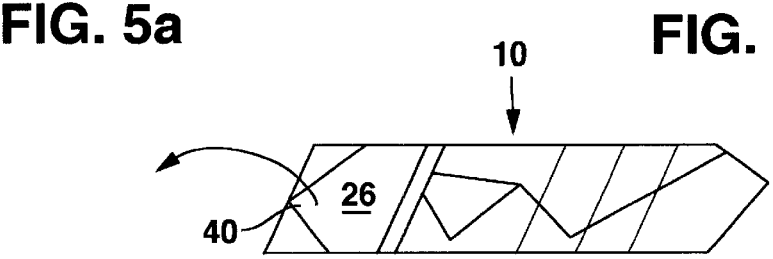
Figure 5D:
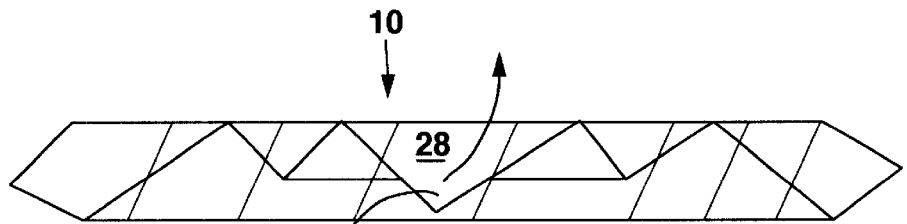

FIG. 4 shows a method for surgical drape deployment 51, and FIGS. 5a–f show a sequence for deployment of one version of the surgical drape 10. The dashed lines in FIGS. 5a–f represent the fold lines in the fabric of the surgical drape 10. Deployment of the surgical drape 10 begins by placing 50 a folded surgical drape 10 over a patient application site 12. Once positioned, the first deployment tab 38 carried on a first portion 24 of the panel 14 is presented for grasping (FIG. 5a). The first deployment tab is grasped 52 and moved away from a fenestration 20 causing the first portion 24 of the panel to deploy 54 (FIG. 5b). Once the first portion 24 is deployed, or partially deployed, the second deployment tab 40 carried on the second portion 26 of the panel 14 is exposed and presented for grasping (FIG. 5c). The second deployment tab is grasped 56 and moved away from the fenestration 20 causing the second portion 26 of the panel to deploy 58 (FIG. 5d). In surgical drapes 10 having only two portions 22, the surgical drape 10 is now fully deployed.

Figure 5E:
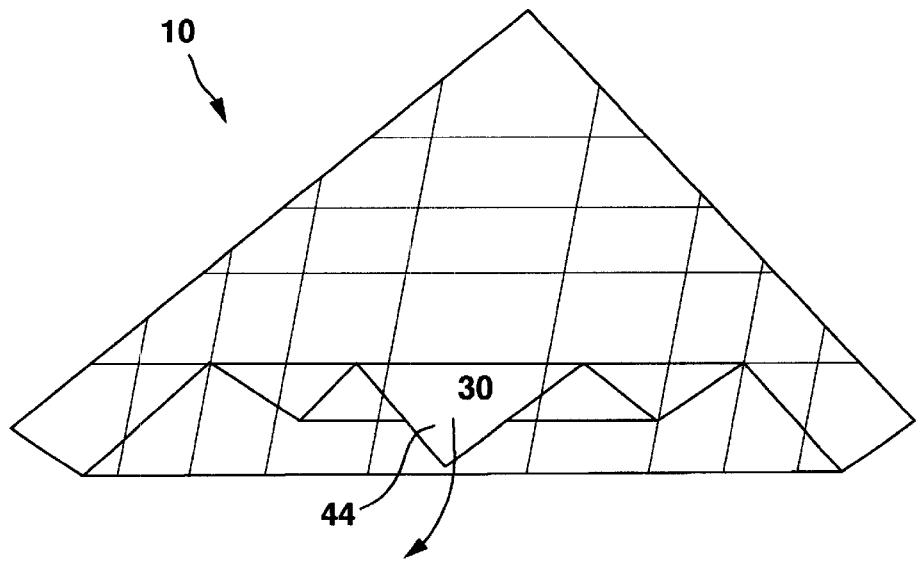
Figure 5F:
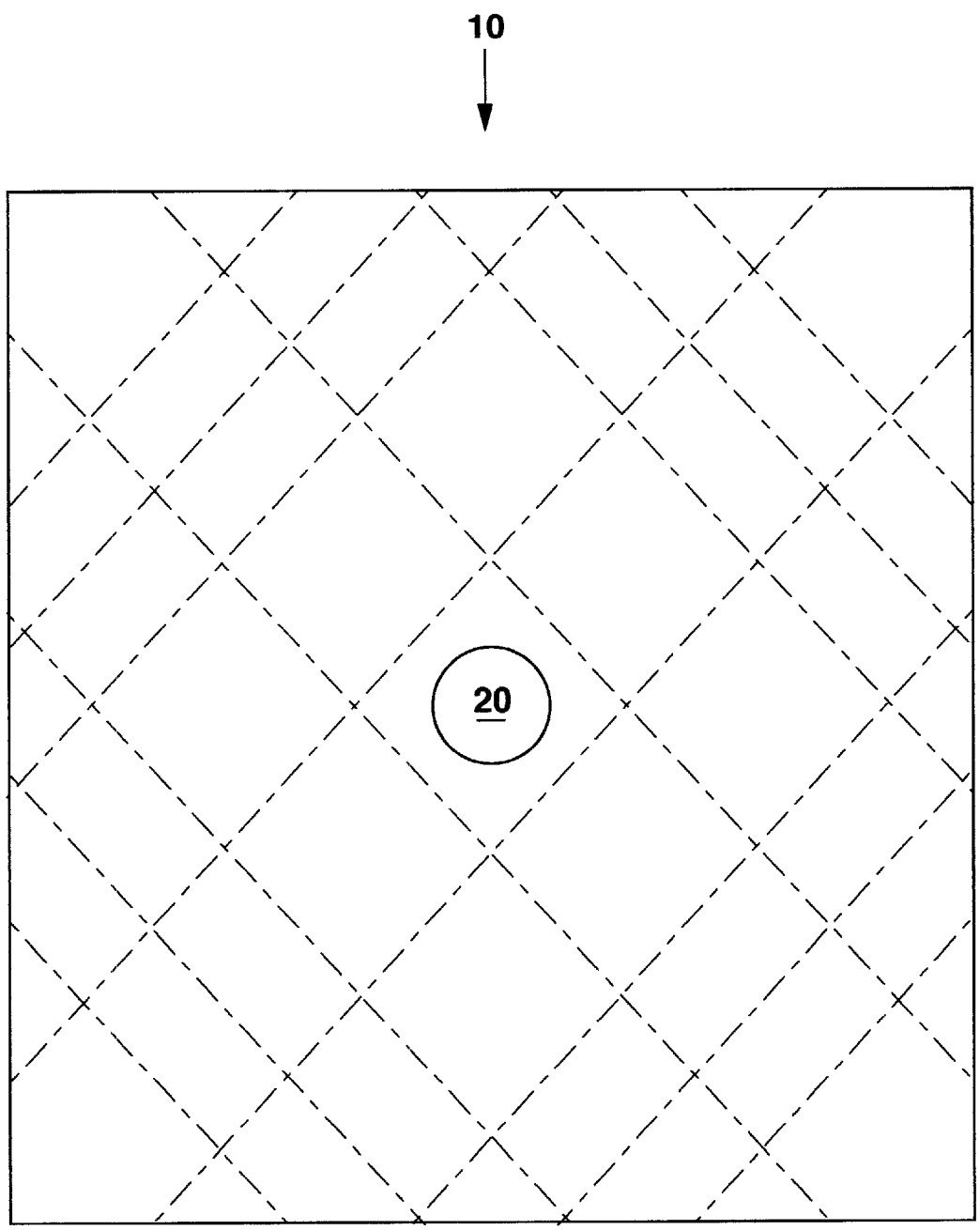

In surgical drapes 10 having more than two portions 22, such as a total of four portions, additional steps are required to deploy the surgical drape 10 as follows. Once the second portion 26 is deployed, or partially deployed, the third deployment tab 42 carried on the third portion 28 of the panel 14 is presented for grasping (FIG. 5d). The third deployment tab is grasped 60 and moved away from the fenestration 20 causing the third portion 28 of the panel to deploy 62 (FIG. 5e). Once the third portion 28 is deployed, or partially deployed, a fourth deployment tab 44 carried on the fourth portion 30 of the panel 14 is presented for grasping. The fourth deployment tab is grasped 64 and moved away from the fenestration 20 causing a fourth portion, and in this illustration a final portion, of the panel to deploy 66 which fully deploys 68 the surgical drape 10 (FIG. 5f). Once all portions 22 of the surgical drape 10 are deployed, the surgical drape 10 is fully deployed 68.

Figure 6:
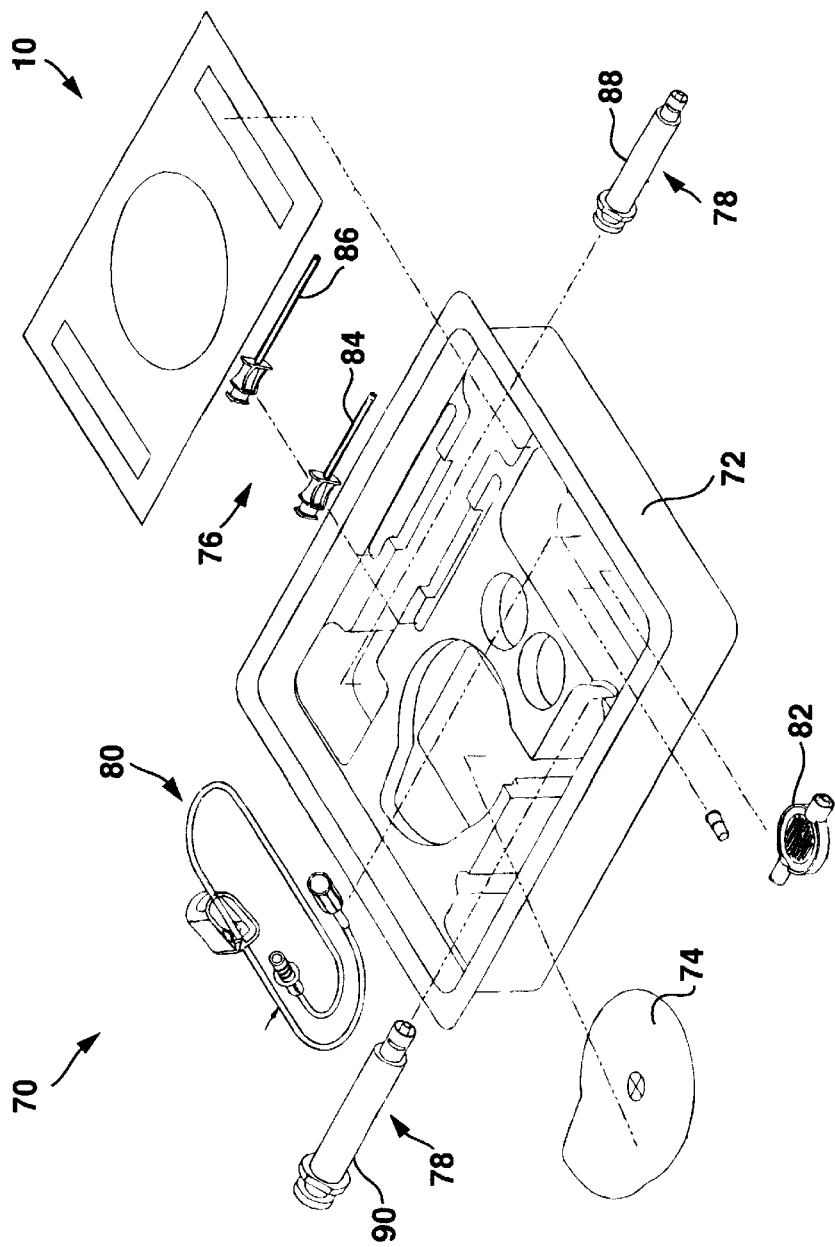
FIG. 6 shows the surgical drape as part of a kit for refilling a drug delivery pump.

FIG. 6 shows the surgical drape 10 as part of a drug delivery pump refill kit 70. Drug delivery pumps typically require periodic servicing such as refilling the pump reservoir. The drug delivery refill kit 70 contains the items needed to refill the pump reservoir for the convenience of the clinician and to reduce risk to the patient by ensuring that the proper items required to refill the pump reservoir are available and organized for the clinician. A drug delivery pump refill kit 70 typically contains a packing tray 72, a refill guide 74, at least one needle 76, at least one syringe 78, an extension connectable to the syringe 80, a filter 82 connectable to the extension, and a surgical drape 10. The drug delivery refill kit 70 can also be configured with a filling needle 84, an emptying needle 86, a filling syringe 88, and an emptying syringe 90. A variety of drug delivery pumps are available from manufacturers such as the IsoMed® and SynchroMed® available from Medtronic, Inc. in Minneapolis, Minn.

Although the invention has been described in detail with reference to certain preferred versions, other versions are possible. For example the surgical drape 10 can take a variety of shapes and can be folded in a variety of patterns to achieve the described advantages. Therefore the spirit and scope of the appended claims should not be limited to the description of the preferred versions described in this disclosure.

What is claimed is:

1. A fenestrated surgical drape configured for in situ deployment, comprising:

a panel having at least two portions, an outer surface, and an inner surface; and a fenestration centrally located in the panel when the panel is folded;

wherein each of the at least two portions has a deployment tab located on a portion distal end corner and the portions are folded over the fenestration so that each deployment tab is accessible and adapted to deploy the portion from over the fenestration to away from the fenestration.

2. The fenestrated surgical drape as in claim 1 wherein the at least two portions have a proximal end that is on or near the fenestration when the at least two portions are folded.

3. The fenestrated surgical drape as in claim 1 where the at least two portions comprise a first portion and a second portion that are folded so the first portion is located over the fenestration and the second portion is located over the first portion.

4. The fenestrated surgical drape as in claim 1 wherein the deployment tab for one of the at least two portions is adapted to deploy the entire portion in a single movement.

5. The fenestrated surgical drape as in claim 1 wherein one of the at least two portions is fully deployed prior to the other of the at least two portions being deployed.

6. The fenestrated surgical drape as in claim 1 wherein the fenestration is sized for a medical device.

7. The fenestrated surgical drape as in claim 1 further comprising a fenestration cover that covers the fenestration until the fenestration cover is removed.

8. The fenestrated surgical drape as in claim 1 wherein the panel is shaped as a tetragon.

9. The fenestrated surgical drape as in claim 8 wherein the panel shaped as a tetragon has four portions.

10. The fenestrated surgical drape as in claim 1 wherein the at least two portions remain folded over the fenestration until the fenestration is located over the application site.

11. The fenestrated surgical drape as in claim 1 further comprising adhesive placed on the inner surface of the main panel near the fenestration.

12. The fenestrated surgical drape as in claim 1 wherein the panel is shaped as a tetragon.

13. The fenestrated surgical drape as in claim 1 wherein the panel shaped as a tetragon has four portions.

14. The fenestrated surgical drape as in claim 1 wherein the fenestration is sized for a medical device.

15. A fenestrated surgical drape configured for in situ deployment, comprising:

a panel having at least two portions, an outer surface, and an inner surface;

a fenestration centrally located in the panel when the panel is folded; and a means for deployment on each of the at least two portions located on a portion distal end corner and the portions are folded over the fenestration so that the means for deployment is accessible and adapted to deploy the portion from over the fenestration to away from the fenestration.

16. A fenestrated surgical drape configured for in situ application, comprising:

a panel having at least two portions, an outer surface, and an inner surface;

a fenestration centrally located in the panel;

wherein the at least two portions are folded over the fenestration so that the inner surface surrounding the fenestration is unobstructed for ease of locating the fenestration over an application site.

17. The fenestrated surgical drape as in claim 16 wherein sterility of the drape is substantially maintained until the at least two portions are deployed.

18. The fenestrated surgical drape as in claim 16 wherein the adhesive is at least one strip of adhesive placed on the inner surface of the main panel.

19. A fenestrated surgical drape configured for in situ application, comprising:

a panel having at least two portions, an outer surface, and an inner surface;

a fenestration centrally located in the panel;

a means for application formed from the at least two portions being folded over the fenestration so that the inner surface surrounding the fenestration is unobstructed for ease of locating the fenestration over an application site.

20. A method of in situ deployment of a fenestrated surgical drape, comprising:

placing a folded surgical drape directly over an application site on a patient;

grasping a first deployment tab carried on a first portion of a panel;

deploying a first portion of the panel by moving the first deployment tab away from a fenestration;

grasping a second deployment tab carried on a second portion of the panel; and, deploying a second portion of the panel by moving the second deployment tab away from the fenestration.

21. The method of in situ deployment of a fenestrated surgical drape as in claim 20, further comprising:

grasping a third deployment tab carried on a third portion of the panel and deploying a third portion of the panel by moving the third deployment tab away from the fenestration.

22. The method of in situ deployment of a fenestrated surgical drape as in claim 21, further comprising:

grasping a fourth deployment tab carried on a fourth portion of the panel and deploying a fourth portion of the panel by moving the fourth deployment tab away from the fenestration.

23. The method of in situ deployment of a fenestrated surgical drape as in claim 20 wherein the at least two portions are folded over the fenestration so that the inner surface surrounding the fenestration is unobstructed for ease of locating the fenestration over an application site.

24. A kit for refilling a drug delivery pump, comprising:

a packing tray;

at least one needle;

at least one syringe connectable to the needle;

a fenestrated surgical drape configured for in situ deployment including a panel having at least two portions, an outer surface, and an inner surface, a fenestration centrally located in the panel, wherein each of the at least two portions has a deployment tab located on a portion distal end and the portions are folded near or on the fenestration so that each deployment tab is accessible and adapted to deploy the portion away from the fenestration.

25. The kit for refilling a drug delivery pump as in claim 24, wherein the at least two portions are folded over the fenestration so that the inner surface surrounding the fenestration is unobstructed for ease of locating the fenestration over an application site.

26. A kit for refilling a drug delivery pump as in claim 24, further comprising:

an extension connectable to the syringe; and, a filter connectable to the extension.

* * * * *